US011471538B2

(12) United States Patent
Favre et al.

(10) Patent No.: US 11,471,538 B2
(45) Date of Patent: Oct. 18, 2022

(54) METHODS AND PHARMACEUTICAL COMPOSITIONS FOR THE TREATMENT OF CANCERS ASSOCIATED WITH ACTIVATION OF THE MAPK PATHWAY

(71) Applicants: INSERM (Institut National de la Santé et de la Recherche Médicale), Paris (FR); Université Paul Sabatier Toulouse III, Toulouse (FR); Centre Hospitalier Universitaire de Toulouse, Toulouse (FR)

(72) Inventors: Gilles Favre, Toulouse (FR); Magdalena Pohorecka, Toulouse (FR)

(73) Assignees: INSERM (INSTITUT NATIONAL DE LA SANTéET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

(*) Notice: Subject to any disclaimer, the term of this patent is extended or adjusted under 35 U.S.C. 154(b) by 45 days.

(21) Appl. No.: 16/485,039

(22) PCT Filed: Feb. 9, 2018

(86) PCT No.: PCT/EP2018/053284
§ 371 (c)(1),
(2) Date: Aug. 9, 2019

(87) PCT Pub. No.: WO2018/146253
PCT Pub. Date: Aug. 16, 2018

(65) Prior Publication Data
US 2019/0365920 A1 Dec. 5, 2019

(30) Foreign Application Priority Data

Feb. 10, 2017 (EP) .................... 17305153

(51) Int. Cl.
*A61K 47/68* (2017.01)
*A61P 35/00* (2006.01)
*A61K 31/437* (2006.01)
*A61K 38/08* (2019.01)
*A61K 39/395* (2006.01)
*C12Q 1/6886* (2018.01)

(52) U.S. Cl.
CPC ........ *A61K 47/6817* (2017.08); *A61K 31/437* (2013.01); *A61K 38/08* (2013.01); *A61K 39/39558* (2013.01); *A61K 47/6849* (2017.08); *A61P 35/00* (2018.01); *C12Q 1/6886* (2013.01); *C07K 2317/51* (2013.01); *C07K 2317/515* (2013.01); *C12Q 2600/118* (2013.01); *C12Q 2600/158* (2013.01)

(58) Field of Classification Search
CPC ............ A61K 47/6817; A61K 47/6849; A61K 31/437; A61K 38/08
See application file for complete search history.

(56) References Cited

U.S. PATENT DOCUMENTS 8,945,570 B2 * 2/2015 Jakobovits .............. A61P 35/00
424/178.1

FOREIGN PATENT DOCUMENTS

| WO | 2012/068562 A2 | 5/2012 | |
|---|---|---|---|
| WO | WO-2014032021 A * | 2/2014 | ......... A61K 47/6811 |
| WO | 2015/041533 A1 | 3/2015 | |
| WO | 2015/041534 A1 | 3/2015 | |
| WO | 2015/095825 A1 | 6/2015 | |

OTHER PUBLICATIONS

Rudikoff et al. Single amino acid substitution altering antigen-binding specificity, PNAS, 79, 1979-1983, Publication Year: 1982 (Year: 1982).*
Morrison et al.; "Development of ASG-15ME, a Novel Antibody-Drug Conugate Targeting SLITRK6, a New Urothelial Cancer Biomarker"; Molecular Cancer Therapeutics, vol. 15, No. 6, Mar. 4, 2016, pp. 1301-1310.
Sanford et al.; "Moloecular Analysis of Upper Tr act and Bladder Urothelial Carcinoma: Results from a Microarray Comparison"; PLOS ONE, vol. 10, No. 8, Aug. 28, 2015, pp. 1-10.

* cited by examiner

*Primary Examiner* — Peter J Reddig
*Assistant Examiner* — Cheng Lu
(74) *Attorney, Agent, or Firm* — WCF IP

(57) ABSTRACT

The response of subjects suffering from cancer to MAPK inhibitors is dramatically impaired by secondary resistances and rapid relapse. So far, the molecular mechanisms driving these resistances are not completely understood. The inventors show that expression of 10 SLITRK6 (SLIT and NTRK-like family, member 6) is induced by a MAPK inhibitor (e.g. Vemurafenib) and the inhibition of its induction in presence of the MAPK inhibitor induces synthetic lethality. Thus, the only inhibition of SLITRK6 by an inhibitor of activity or expression should potentiate the antitumor effect of the MAPK inhibitors and avoid the emergence of a resistance to those compounds. Furthermore the specific expression of 15 SLITRK6 also paves the way of strategies based on depletion of the residual cancer cells by targeting them with anti-SLITRK6 antibodies capable of mediating ADCC or antibody-drug conjugates binding to SLITRK6.

Figure 1A:
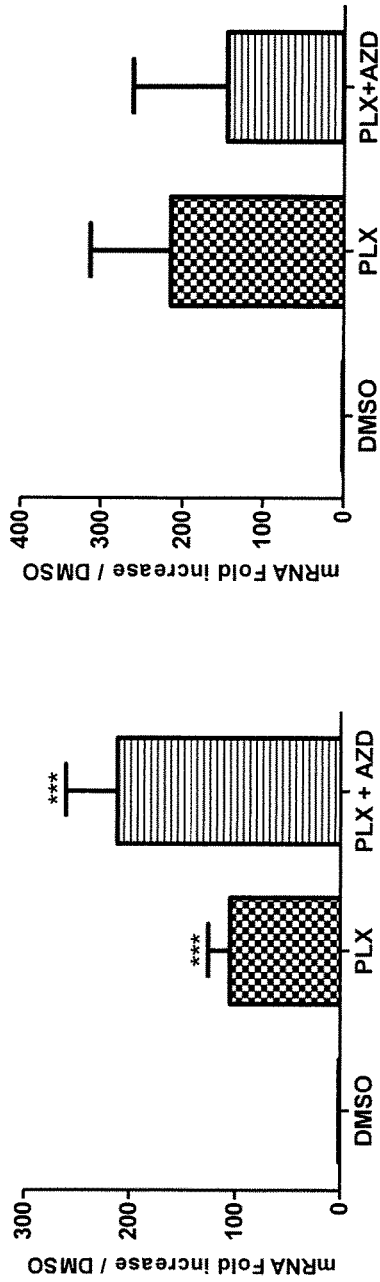

12 Claims, 8 Drawing Sheets
Specification includes a Sequence Listing.

METHODS AND PHARMACEUTICAL COMPOSITIONS FOR THE TREATMENT OF CANCERS ASSOCIATED WITH ACTIVATION OF THE MAPK PATHWAY

FIELD OF THE INVENTION

The present invention relates to methods and pharmaceutical compositions for the treatment of cancers associated with activation of the MAPK pathway.

BACKGROUND OF THE INVENTION

The MAPK (mitogen-activated protein kinase) pathway has been shown to play a key role in a number of normal physiological processes such as cellular metabolism, cell cycle progression, cell death, and neurological function. The MAPK pathway is constitutively activated in a significant proportion of human tumors often through gain-of-function mutations in RAS or RAF gene family members. For instance, mutations in the MAPK pathway have been shown to be very important in melanoma development in that up to 90% of melanomas and benign melanocytic neoplasms carry activating mutations in B-RAF, K-RAS, or N-RAS. Activating mutations in BRAF indeed occur in 7-8% of all solid tumors and in 60% of malignant melanomas, 8-15% of colorectal cancer and 3% of cases of pancreatic carcinoma and 2% of lung cancers. Melanoma is the most aggressive skin cancer. It often induces metastasis and its incidence is rapidly growing and continues to rise alarmingly. Surgery is curative in nearly all cases before metastatic stage, but when metastasis appears, surgery, radiotherapy and conventional chemotherapy have little curative effects and subject survival is usually short. Therefore several promising new therapies have been developed essentially based on targeted chemotherapy using MAPK inhibitors and in particular specific anti-BRAFV600 inhibitors (e.g. Vemurafenib (PLX4032) and Dabrafenib). Preclinical studies indicate that Vemurafenib and Dabrafenib block the mutated BRAF protein, inducing cell growth arrest and cell death in a low proportion of tumors carrying this mutation. Clinical trials of Vemurafenib and Dabrafenib have shown therapeutic effect in more than 50% of subjects with BRAFV600E positive metastatic melanomas. More recently, it has been shown that the combination of BRAF inhibitor and MEK inhibitor improved tumor response and induced an increase overall survival of the BRAF mutated subject leading to propose this combination as the first line therapy in such subjects. However, unfortunately, in most subject's melanoma cells outbreak and progress again once resistance to MAPK inhibitors is acquired. Therefore, identification and characterization of unknown pathways mediating resistance to those inhibitors are essential for the rational design of targeted strategies to prevent and overcome said resistance across this entire population of subjects.

SUMMARY OF THE INVENTION

The present invention relates to methods and pharmaceutical compositions for the treatment of cancers associated with activation of the MAPK pathway. In particular, the present invention is defined by the claims.

DETAILED DESCRIPTION OF THE INVENTION

The response to MAPK inhibitors is dramatically impaired by secondary resistances and rapid relapse. So far, the molecular mechanisms driving these resistances are not completely understood. The inventors have shown that in BRAF-mutant melanoma cells, inhibition of BRAF or its target MEK induces RHOB expression by a mechanism that depends on the transcription factor c-Jun (Oncotarget. 2015 Jun. 20; 6(17):15250-64). More particularly their findings reveal that BRAF inhibition activates a c-Jun/RHOB/AKT pathway that promotes tumor cell survival and further support a role of this pathway in the resistance of melanoma to MAPK inhibitors. Now the inventors show that activation of c-Jun induces the expression of SLITRK6 (SLIT and NTRK-like family, member 6). In particular, the inventors demonstrate that SLITRK6 is induced by a MAPK inhibitor (e.g. Vemurafenib) and the inhibition of its induction leads to apoptotic cell death as in the A375 line. Thus, the only inhibition of SLITRK6 by an inhibitor of activity or expression should potentiate the antitumor effect of MAPK inhibitors and avoid the emergence of a resistance to those compounds. Furthermore the specific expression of SLITRK6 also paves the way of strategies based on depletion of the residual cancer cells by targeting them with anti-SLITRK6 antibodies capable of mediating ADCC or antibody-drug conjugates binding to SLITRK6.

Accordingly, the first object of the present invention relates to a method of treating a cancer associated with activation of the MAPK pathway in a subject in need thereof comprising administering to the subject a therapeutically effective combination comprising at least one MAPK inhibitor and an agent capable of inducing cell death of SLITRK6 expressing cancer cells.

A further object of the present invention relates to a method of treating a cancer resistant to MAPK inhibitors in a subject in need thereof comprising administering to the subject a therapeutically effective amount of an agent capable of inducing cell death of SLITRK6 expressing cancer cells.

A further object of the present invention relates to a method for enhancing the potency of a MAPK inhibitor administered to a subject suffering from a cancer as part of a treatment regimen, the method comprising administering to the subject a pharmaceutically effective amount of an agent capable of inducing cell death of SLITRK6 expressing cancer cells in combination with at least one MAPK inhibitor.

A further object of the present invention relates to a method of preventing resistance to an administered MAPK inhibitor in a subject suffering from a cancer comprising administering to the subject a therapeutically effective amount of an agent capable of inducing cell death of SLITRK6 expressing cancer cells.

As used herein, the expression "MAPK pathway" also known as the "RAS-RAF-MEK-ERK pathway" has its general meaning in the art and refers to chain of proteins in the cell that communicates a signal from a receptor on the surface of the cell to the DNA in the nucleus of the cell. The signal starts when a signalling molecule binds to the receptor on the cell surface and ends when the DNA in the nucleus expresses a protein and produces some change in the cell, such as cell division.

In some embodiments, the subject suffers from a cancer showing an increased activation of the MAPK pathway (i.e. "cancer associated with activation of the MAPK pathway"). As used herein, increased expression or activity is understood as an expression level or activity level which is at least 10%, at least 20%, at least 30%, at least 40%, at least 50%, at least 100%, at least 200%, at least 300% or more with respect to a reference expression level or to a reference activity level. Methods for determining whether the expression level of a given component of the MAPK pathway is increased are well-known in the art and include methods based on the determination of the mRNA levels of the corresponding component (e.g., Northern blot, RT-PCR and the like) and methods based on the determination of the protein levels of the corresponding component (e.g., ELISA, Western blot, etc.). Methods for determining whether the activity of one or more components of the MAPK pathway is increased are based on the determination of the activity of the different components and are widely known to the skilled person. Suitable methods for determining the activity of the MAPK pathway include, for instance, the detection of phosphorylated ERK (MAPK) protein as well as the ratio of phosphoERK to ERK.

In some embodiments, the subject suffers from a cancer characterized by the presence of least one mutation in a protein involved in the MAPK pathway. Typically, the cancer is characterized by at least one mutation in a tyrosine kinase receptor (e.g. FGFR1, FGFR2, FGFR3, EGFR, HER2, IGF-1R cMET . . . ), BRAF, RAS, CRAF, CCND1, CDK4, MAP2K1, MAP2K2, NRAS, KRAS HRAS, PTEN, PIK3CA, and P16. In some embodiments, the subject suffers from a RAS-mutated cancer. As used herein, the term "RAS" represents any member of the RAS family of proteins or mutants thereof. Ras family proteins include, but are not limited to, HRAS, KRAS and NRAS, as well as other members of this subfamily as well: DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASLIA; RASL11B; RASL12; REM1; REM2; RERG; RERGL; RRAD; RRAS; RRAS2 (Wennerberg et al., The Ras superfamily at a glance, J. Cell. Sci., 2005, 118 (Pt 5), 843-846). Accordingly, the expression "mutated-RAS cancer" refers to a cancer in which the cancer cells comprise an activating mutation in a Ras protein. In particular, the subject suffers from a NRAS-mutated cancer. A number of mutations in NRAS are known and typically include Q61R, Q61K, Q61H, Q61L, Q61N, Q61E, Q61P, A146T, A146P, or A146V. In some embodiments, the subject suffers from a RAF-mutated cancer. As used herein, the term "RAF" represents any member of the Raf family of proteins or mutants thereof. RAFfamily proteins include, but are not limited to A-RAF, B-RAF and C-RAF. Accordingly, the expression "mutated-RAF cancer" refers to a cancer in which the cancer cells comprise an activating mutation in a Raf protein. In particular, the subject suffers from a BRAF-mutated cancer. A number of mutations in BRAF are known. In particular, the V600E mutation is prominent. Other mutations which have been found are R461I, I462S, G463E, G463V, G465A, G465E, G465V, G468A, G468E, N580S, E585K, D593V, F594L, G595R, L596V, T598I, V599D, V599E, V599K, V599R, V600E, A727V, and most of these mutations are clustered to two regions: the glycine-rich P loop of the N lobe and the activation segment and flanking regions. As is known in the art, several PCR and/or sequencing based methods are known for use in detecting mutations in the MAPK pathway and are presented in several research articles and US patents including, but not limited to, Brose, et al. Cancer Research 62:6997-7000 (2002), Solit et al, Cancer Research 70(14): 5901-5911 (1010), Xu, et al. Cancer research 63:4561-4567 (2003), as well as U.S. Pat. No. 7,745,128, and several commercially available kits (see Dxs Diagnostic Innovations, Applied Biosystems, and Quest diagnostics).

In some embodiments, the subject suffers from a cancer selected from the group consisting of melanoma, multiple myeloma, lung cancer, colorectal cancer, thyroid carcinoma, blood cancer, leukemia, and lymphoma. In particular, the subject suffers from melanoma, in particular metastatic melanoma. As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found. 40-60% of melanomas carry an activating mutation BRAF.

As used herein, the term "MAPK inhibitor" refers to any compound that is currently known in the art or that will be identified in the future, and includes any chemical entity that, upon administration to a subject, results in inhibition the MAPK pathway in the cancer cells of the subject. MAPK inhibitors include but are not limited to low molecular weight inhibitors, antibodies or antibody fragments, antisense constructs, small inhibitory RNAs (i.e. RNA interference by dsRNA; RNAi), and ribozymes. In some embodiments, the MAPK inhibitor is a small organic molecule. MAPK inhibitors include, for example, RAS inhibitors, RAF inhibitors, or MEK inhibitors.

A MEK inhibitor is a compound that shows MEK inhibition when tested in the assays titled, "Enzyme Assays" in U.S. Pat. No. 5,525,625, column 6, beginning at line 35. The complete disclosure of U.S. Pat. No. 5,525,625 is hereby incorporated by reference. Specifically, a compound is an MEK inhibitor if a compound shows activity in the assay titled, "Cascade Assay for Inhibitors of the MAP Kinase Pathway," column 6, line 36 to column 7, line 4 of the U.S. Pat. No. 5,525,625 and/or shows activity in the assay titled, "In Vitro MEK Assay" at column 7, lines 4 to 27 of the above-referenced patent. Alternatively, MEK inhibition can be measured in the assay described in WO 02/06213 A1, the complete disclosure of which is hereby incorporated by reference. MEK inhibitors include, for example, ARRY-142886 (also known as AZD6244; Array BioPharma/Astrazeneca), PD-184352 (also known as CI-1040; Pfizer), XL518 (Exelixis), PD0325901 (Pfizer), PD-98059 (Pfizer), MEK1 (EMD), or 2-(2-amino-3-methoxyphenyl)-4-oxo-4H-[1]benzopyran and 2-(2-chloro-4-iodo-phenylamino)-N-cyclopropylmethoxy-3,4-difluoro-benzamide. Specific preferred examples of MEK inhibitors that can be used according to the present invention include ARRY-142886, PD-184352, PD-98059, PD-0325901, XL518, or MEK1.

RAS inhibitors include, for example, BMS-214662 (Bristol-Myers Squibb), SCH 66336 (also known as lonafarnib; Schering-Plough), L-778,123 (Merck), R115777 (also known as Zarnestra or Tipifamib; Johnson and Johnson), and 6-[(4-chloro-phenyl)-hydroxy-(3-methyl-3H-imidazol-4-yl)-methyl]-4-(3-ethynyl-phenyl)-1-methyl-1H-quinolin-2-one (OSIPharmaceuticals, Inc.). Ras inhibitors disclosed in U.S. Pat. Nos. 6,150,377 and 6,645,982 are included. The complete disclosures of U.S. Pat. Nos. 6,150,377 and 6,645, 982 are incorporated by reference.

Suitable RAF inhibitor and in particular BRAF inhibitors may include, but are not limited to, 1,2-di-cyclyl substituted alkyne compounds or derivatives; 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine); 2,6-disubstituted quinazoline, quinoxaline, quinoline, and isoquinoline compounds or derivatives; 4-amino-5-oxo-8-phenyl-5H-pyrido-[2,3-D]-pyrimidine compounds or derivatives; 4-amino-thieno[3,2-C]pyridine-7-carboxylic acid compounds or derivatives; 5-(4-aminophenyl)-isoquinoline compounds or derivatives; benzene sulfonamide thiazole compounds or derivatives; benzimidazole compounds or derivatives; bicyclic compounds or derivatives; bridged, bicyclic heterocyclic or spiro bicyclic heterocyclic derivatives of pyrazolo[1,5-a]pyrimidine compounds or derivatives; cinnamide and hydro-cinnamide compounds or derivatives; di-substituted imidazole compounds or derivatives; fused tricyclic pyrazolo[1,5-a]pyrimidine compounds or derivatives; heteroaryl compounds or derivatives; heterocyclic compounds or derivatives; 1H-benzo [D] imidazole compounds or derivatives; imidazo [4,5-B] pyridine compounds or derivatives; N-(6-aminopytidin-3-yl)-3-(sulfonamido) benzamide compounds or derivatives; N-[3-(1-amino-5,6,7,8-tetrahydro-2,4,4B-triazafluoren-9-yl)-phenyl] benzamide compounds or derivatives; nitrogen-containing bicyclic heteroaryl compounds or derivatives; N-oxides of heterocyclic substituted bisarylurea compounds or derivatives; omega-carboxylaryl substituted diphenyl urea compounds or derivatives; oxazole compounds or derivatives; phenethylamide compounds or derivatives; phenylsulfonamide-substituted, pyrazolo[1,5-a]pyrimidine compounds or derivatives; phenyltriazole compounds or derivatives; heterocyclic compounds or derivatives; 1 h-pyrazolo[3,4-b] pyridine compounds or derivatives; purine compounds or derivatives; pyrazole [3,4-B] pyridine compounds or derivatives; pyrazole compounds or derivatives; pyrazoline compounds or derivatives; pyrazolo [3,4-b] pyridines, pyrrolo [2, 3-b] pyridine compounds or derivatives; pyrazolo [3,4-d]pyrimidine compounds or derivatives; pyrazolo [5,1-c] [1,2,4]triazine compounds or derivatives; pyrazolyl compounds or derivatives; pyrimidine compounds or derivatives; pyrrol compounds or derivatives; pyrrolo [2,3-B] pyridine compounds or derivatives; substituted 6-phenyl-pyrido [2, 3-D] pyrimidin-7-ones compounds or derivatives; substituted benzazole compounds or derivatives; substituted benzimidazole compounds or derivatives; substituted bisaryl-urea compounds or derivatives; thienopyridine compounds or derivatives; thienopyrimidine, thienopyridine, or pyrrolopyrimidine compounds or derivatives; thiophene amide compounds or derivatives, and any other suitable aryl and/or heteroaryl compounds or derivatives. Several patents and patent applications disclose exemplar BRAF inhibitors that may be used in accordance with the embodiments described herein including, but not limited to, International Patent Application Publication Nos WO2011117381, WO2011119894, WO2011117381, WO2011097594, WO2011097526, WO2011085269, WO2011090738, WO2011025968, WO2011025927, WO2011023773, WO2011028540, WO2010111527, WO2010104973, WO2010100127, WO2010078408, WO2010065893, WO2010032986, WO2009115572, WO2009108838, WO2009111277, WO2009111278, WO2009111279, WO2009111280, WO2009108827, WO2009111260, WO2009100536, WO2009059272, WO2009039387, WO2009021869, WO2009006404, WO2009006389, WO2008140850, WO2008079277, WO2008055842, WO2008034008, WO2008115263, WO2008030448, WO2008028141, WO2007123892, WO2007115670, WO2007090141, WO2007076092, WO2007067444, WO2007056625, WO2007031428, WO2007027855, WO2007002433, WO2007002325, WO2006125101, WO2006124874, WO2006124780, WO2006102079, WO2006108482, WO2006105844, WO2006084015, WO2006076706, WO2006050800, WO2006040569, WO2005112932, WO2005075425, WO2005049603, WO2005037285, WO2005037273, WO2005032548; and U.S. Pat. Nos. 8,642,759, 8,557,830, 8,504,758, 7,863,288, 7,491,829, 7,482,367, and 7,235,576; the specifications of all of which are hereby incorporated by reference as if fully set forth herein. In some embodiments, the BRAF inhibitor is selected from a group of molecules selected from AMG542, ARQ197, ARQ736, AZ628, CEP-32496, GDC-0879, GSK1 120212, GSK21 18436 (dabrafenib, Tafinlar®), LGX818 (encorafenib), NMS-P186, NMS-P349, NMS-P383, NMS-P396, NMS-P730, PLX3603 (R05212054), PLX4032 (vemurafenib, Zelboraf®), PLX4720 (Difluorophenyl-sulfonamine), PF-04880594, PLX4734, RAF265 (CHIR-265), R04987655, SB590885, sorafenib, sorafenib tosylate, or XL281 (BMS-908662). In some embodiments, one skilled in the art may generate or identify novel BRAF inhibitors using in vitro, in vivo, in silico, or other screening methods known in the art. For example, a BRAF inhibitor of wild type BRAF may be identified from a training set of small molecules, peptides, or nucleic acids using an assay for detecting phosphorylation of molecules which are downstream from BRAF in the MAPK signaling cascade (e.g., MEK and/or ERK). The BRAF inhibitor may act to suppress or inhibit BRAF expression and/or signaling function, thereby reducing phosphorylation of MEK and ERK. Several phosphorylation assays are available which could be used in such embodiments including, but not limited to, kinase activity assays (e.g., those sold by R&D Systems®, Promega®, Life Technologies®); phospho-specific antibodies for use with immunoassays such as western blots, enzyme-linked immunosorbent assays (ELISA), flow cytometry, immunocytochemistry, immunohistochemistry; mass spectrometry, proteomics, and phospho-protein multiplex assays.

In some embodiments, the subject is preferentially administered with a combination of BRAF inhibitor with a MEK inhibitor.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein the term "resistance to MAPK inhibitors" is used in its broadest context to refer to the reduced effectiveness of at least one MAPK inhibitor (e.g. a BRAF inhibitor alone or a combination comprising a BRAF inhibitor and a MEK inhibitor) to inhibit the growth of a cell, kill a cell or inhibit one or more cellular functions, and to the ability of a cell to survive exposure to an agent designed to inhibit the growth of the cell, kill the cell or inhibit one or more cellular functions. The resistance displayed by a cell may be acquired, for example by prior exposure to the agent, or may be inherent or innate. The resistance displayed by a cell may be complete in that the agent is rendered completely ineffective against the cell, or may be partial in that the effectiveness of the agent is reduced. Accordingly, the term "resistant" refers to the repeated outbreak of cancer, or a progression of cancer independently of whether the disease was cured before said outbreak or progression.

As used herein, the term "SLITRK6" has its general meaning in the art and refers to SLIT and NTRK like family member 6 encoded by SLITRK6 gene (Gene ID: 84189). The term SLITRK6 is also known as DFNMYP. This gene encodes a member of the SLITRK protein family. Members of this family are integral membrane proteins that are characterized by two N-terminal leucine-rich repeat (LRR) domains and a C-terminal region that shares homology with TRK neurotrophin receptors. This protein was originally described as a regulator of neurite outgrowth required for normal hearing and vision. Exemplary human nucleic and amino acid sequences are represented respectively by the NCBI reference sequences NM_032229.2 and NP_115605.2. As used herein, the term "SLITRK6 expressing cancer cells" refers to cancer cells that express SLITRK6 following administration of BRAF inhibitor.

As used herein, the term "agent capable of inducing cell death of SLITRK6 expressing cancer cells" refers to any molecule that under cellular and/or physiological conditions is capable of inducing cell death of SLITRK6 expressing cancer cells. In particular, the agent is capable of inducing apoptosis of SLITRK6 expressing cancer cells. In some embodiments, the agent is capable of depleting SLITRK6 cancer cells. As used herein, the term "depletion" with respect to cancer cells, refers to a measurable decrease in the number of SLITRK6 expressing cancer cells in the subject. The reduction can be at least about 10%, e.g., at least about 20%, 30%, 40%, 50%, 60%, 70%, 80%, 90%, 95%, 96%, 97%, 98%, 99%, or more. In some embodiments, the term refers to a decrease in the number of SLITRK6 cancer cells in the subject below detectable limits.

In some embodiments, the agent is an inhibitor of SLITRK6 expression. The inventors have indeed shown that inhibition of SLITRK6 can trigger apoptosis of cancer cells. An "inhibitor of expression" refers to a natural or synthetic compound that has a biological effect to inhibit the expression of a gene. In some embodiments, said inhibitor of gene expression is a siRNA, an antisense oligonucleotide or a ribozyme. For example, anti-sense oligonucleotides, including anti-sense RNA molecules and anti-sense DNA molecules, would act to directly block the translation of SLITRK6 mRNA by binding thereto and thus preventing protein translation or increasing mRNA degradation, thus decreasing the level of SLITRK6, and thus activity, in a cell. For example, antisense oligonucleotides of at least about 15 bases and complementary to unique regions of the mRNA transcript sequence encoding SLITRK6 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. SLITRK6 gene expression can be reduced by contacting a subject or cell with a small double stranded RNA (dsRNA), or a vector or construct causing the production of a small double stranded RNA, such that SLITRK6 gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing SLITRK6. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone non homologous end-joining (NHEJ) and the high-fidelity homology-directed repair (HDR). In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from *Streptococcus pyogenes*. The CRISPR/Cas9 system has been described in U.S. Pat. No. 8,697,359 B1 and US 2014/0068797. In some embodiment, the endonuclease is CRISPR-Cpf1 which is the more recently characterized CRISPR from *Provotella* and *Francisella* 1 (Cpf1) in Zetsche et al. ("Cpf1 is a Single RNA-guided Endonuclease of a Class 2 CRISPR-Cas System (2015); Cell; 163, 1-13).

In some embodiments, the agent is a small organic molecule which inhibits the kinase activity of SLITRK6 or all molecule that can inhibit SLITRK6 function.

In some embodiments, the agent is an antibody having binding affinity for SLITRK6. In some embodiments, the agent is an antibody directed against the extracellular domain of SLITRK6. In some embodiments, the antibody leads to the inhibition of SLITRK6 activity. In some embodiments, the antibody leads to the internalisation of SLITRK6 in cancer cells. In some embodiments, the antibody leads to the depletion of cancer cells (e.g. an antibody-drug conjugate as described herein after).

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

As used herein the term "bind" indicates that the antibody has affinity for the surface molecule. The term "affinity", as used herein, means the strength of the binding of an antibody to an epitope. The affinity of an antibody is given by the dissociation constant Kd, defined as $[Ab] \times [Ag]/[Ab-Ag]$, where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure.

The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference.

In some embodiments, the antibody comprises heavy and light chain variable regions of an antibody designated Ha15-10ac12 produced by a Chinese Hamster Ovary (CHO) cell deposited under the American Type Culture Collection (ATCC) Accession No.: PTA-13102. The heavy chain variable region of Ha15-10ac12 has the amino acid as set forth in SEQ ID NO: 1, and the light chain variable region of Ha15-10ac12 has the amino acid sequence as set forth in SEQ ID NO:2

```
                                          SEQ ID NO: 1
QVQLVESGGGVVQPGRSLRLSCAASGFTFSSYGMHWVRQAPGKGLEWVAV

IWYDGSNQYYADSVKGRFTISRDNSKNTLFLQMHSLRAEDTAVYYCARGL

TSGRYGMDVWGQGTTVTVSS
                                          SEQ ID NO: 2
DIVMTQSPLSLPVTPGEPASISCRSSQSLLLSHGFNYLDWYLQKPGQSPQ

LLIYLGSSRASGVPDRFSGSGSGTDFTLKISRVEAEDVGLYYCMQPLQIP

WTFGQGTKVEIKR
```

In some embodiments, the antibody contains the heavy chain CDRs of the heavy chain variable region of HA15-10ac12 (SEQ ID NO:1). In some embodiments, the antibody of the present invention comprises the light chain CDRs of the light chain variable region of HA15-10ac12 (SEQ ID NO:2).

In some embodiments, the antibody suitable for depletion of cancer cells mediates antibody-dependent cell-mediated cytotoxicity. As used herein the term "antibody-dependent cell-mediated cytotoxicity" or 'ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. While not wishing to be limited to any particular mechanism of action, these cytotoxic cells that mediate ADCC generally express Fc receptors (FcRs).

As used herein "Fc region" includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc region. The amino acid sequence of a non-naturally occurring Fc region (also referred to herein as a "variant Fc region") comprises a substitution, insertion and/or deletion of at least one amino acid residue compared to the wild type amino acid sequence. Any new amino acid residue appearing in the sequence of a variant Fc region as a result of an insertion or substitution may be referred to as a non-naturally occurring amino acid residue. Note: Polymorphisms have been observed at a number of Fc positions, including but not limited to Kabat 270, 272, 312, 315, 356, and 358, and thus slight differences between the presented sequence and sequences in the prior art may exist.

The terms "Fc receptor" or "FcR" are used to describe a receptor that binds to the Fc region of an antibody. The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998). As used herein, the term Effector cells" are leukocytes which express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

In some embodiments, the antibody suitable for depletion of cancer cells is a full-length antibody. In some embodiments, the full-length antibody is an IgG1 antibody. In some embodiments, the full-length antibody is an IgG3 antibody.

In some embodiments, the antibody suitable for depletion of cancer cells comprises a variant Fc region that has an increased affinity for FcγRIA, FcγRIIA, FcγRIIB, FcγRIIIA, FcγRIIIB, and FcγRIV. In some embodiments, the antibody of the present invention comprises a variant Fc region comprising at least one amino acid substitution, insertion or deletion wherein said at least one amino acid residue substitution, insertion or deletion results in an increased affinity for FcγRIA, FcγRIIA, FcγRIIB, FcγRIIIA, FcγRIIIB, and FcγRIV, In some embodiments, the antibody of the present invention comprises a variant Fc region comprising at least one amino acid substitution, insertion or deletion wherein said at least one amino acid residue is selected from the group consisting of: residue 239, 330, and 332, wherein amino acid residues are numbered following the EU index. In some embodiments, the antibody of the present invention comprises a variant Fc region comprising at least one amino acid substitution wherein said at least one amino acid substitution is selected from the group consisting of: S239D, A330L, A330Y, and I332E, wherein amino acid residues are numbered following the EU index.

In some embodiments, the glycosylation of the antibody suitable for depletion of cancer cells is modified. For example, an aglycosylated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the human monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the human monoclonal antibodies of the present invention can be produced in yeasts or filamentous fungi engineered for mammalian-like glycosylation pattern and capable of producing antibodies lacking fucose as glycosylation pattern (see for example EP1297172B1 In some embodiments, the antibody suitable for depletion of cancer cells mediated complement dependant cytotoxicity. "Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

In some embodiments, the antibody suitable for depletion of cancer cells mediates antibody-dependent phagocytosis. As used herein, the term "antibody-dependent phagocytosis" or "opsonisation" refers to the cell-mediated reaction wherein nonspecific cytotoxic cells that express FcγRs recognize bound antibody on a target cell and subsequently cause phagocytosis of the target cell.

In some embodiments, the antibody suitable for depletion of cancer cells is a multispecific antibody comprising a first antigen binding site directed against SLITRK6 and at least one second antigen binding site directed against an effector cell as above described. In said embodiments, the second antigen-binding site is used for recruiting a killing mechanism such as, for example, by binding an antigen on a human effector cell. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs. In some embodiments, the second binding site binds to a Fc receptor as above defined. In some embodiments, the second binding site binds to a surface molecule of NK cells so that said cells can be activated. In some embodiments, the second binding site binds to NKp46. Exemplary formats for the multispecific antibody molecules of the present invention include, but are not limited to (i) two antibodies cross-linked by chemical heteroconjugation, one with a specificity to a specific surface molecule of ILC and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In some embodiments, the antibody suitable for depletion of cancer cells is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody suitable for depletion of cancer cells is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In some embodiments, the antibody suitable for depletion of cancer cells is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody suitable for depletion of cancer cells is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3): 154-169; Howard P. W. et al., Bioorg Med Chem Lett 2009; 19: 6463-6466 and Sagnou et al., Bioorg Med Chem Lett 2000; 10(18): 2083-2086.

In some embodiments, the antibody suitable for depletion of cancer cells is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody suitable for depletion of cancer cells is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

In some embodiments, the antibody suitable for depletion of cancer cells is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

Techniques for conjugating molecule to antibodies, are well-known in the art (See, e.g., Amon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target humanepidermal growth factor receptor 2-positive breast cancer. Clin. Cancer Res. 16, 4769-4778). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site—specifically conjugated to the Fc-containing polypeptide through the acyl donor glutamine—containing tag or the accessible/exposed/reactive endogenous glutamine (WO 2012059882).

As used herein, the term "combination" is intended to refer to all forms of administration that provide a first drug together with a further (second, third . . . ) drug. The drugs may be administered simultaneous, separate or sequential and in any order. Drugs administered in combination have biological activity in the subject to which the drugs are delivered. Within the context of the invention, a combination thus comprises at least two different drugs, and wherein one drug is at least a MAPK-inhibitor (e.g. a BRAF inhibitor or a BRAF inhibitor+a MEK inhibitor) and wherein the other drug is at least an agent capable of inducing cell death of SLITRK6 expressing cancer cells. In some instance, the combination of the present invention results in the synthetic lethality of the cancer cells.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drug of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

A further object of the present invention relates to a method of determining relapse in subject suffering from a cancer after a treatment regimen comprising administration of a MAPK inhibitor comprising i) detecting the expression of SLITRK6 in a tumor sample obtained from the subject and ii) concluding that the subject relapses when the expression of SLITRK6 is detected at step i).

The term "relapse" as used herein refers to reappearance of the cancer after an initial period of responsiveness (e.g., complete response or partial response). The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. More generally, a response (e.g., complete response or partial response) can involve the absence of detectable MRD (minimal residual disease). In some embodiments, the initial period of responsiveness lasts at least 1, 2, 3, 4, 6, 8, 10, or 12 months; or at least 1, 2, 3, 4, or 5 years.

As used herein, the term "tumor sample" means any tissue tumor sample derived from the subject. Said tissue sample is obtained for the purpose of the in vitro evaluation. In some embodiments, the tumor sample may result from the tumor resected from the subject. In some embodiments, the tumor sample may result from a biopsy performed in the primary tumor of the subject or performed in metastatic sample distant from the primary tumor of the subject. In some embodiments, the tumor sample is a sample of circulating tumor cells. As used herein, the term "circulating tumor cell" or "CTC" refers to a cancer cell derived from a cancerous tumor that has detached from the tumor and is circulating in the blood stream of the subject. Typically the CTCs are isolated from the blood sample using a filter and/or a marker based method. For example, CTCs can be isolated using an anti-EpCAM antibody to magnetically capture CTCs expressing this antigen on their surfaces with for example the CellSearchR system (Scher et al., 2005; Berthold et al., 2008; Madan et al., 2011; Fleming et al., 2006; Gulley and Drake, 2011; Bubley et al., 1999; Scher et al., 2008). Other approaches include for example detecting the presence of circulating nucleic acids (Schwarzenbach et al., 2011), on immunohistochemistry with anti-cytokeratin 8 and 18 antibodies that are also used in combination with the anti-EpCAM antibodies, or on CTC-chips as well as the EPISPOT test, which depletes CD45 cells first and examines the remaining cells. In addition, collagen adhesion matrix assays (CAM assays) can be used (for a review on these methods, see Doyen et al., 2011).

Detection of expression of SLITRK6 may be performed by any method well known in the art.

In some embodiments, the detection is performed by immunodetection such as immunohistochemistry or immunofluorescence. For instance, immunohistochemistry typically includes the following steps i) fixing the tumor tissue sample with formalin, ii) embedding said tumor tissue sample in paraffin, iii) cutting said tumor tissue sample into sections for staining, iv) incubating said sections with the binding partner specific for the marker (i.e. SLITRK6), v) rinsing said sections, vi) incubating said section with a secondary antibody typically biotinylated and vii) revealing the antigen-antibody complex typically with avidin-biotin-peroxidase complex. Accordingly, the tumor tissue sample is firstly incubated the binding partners. After washing, the labeled antibodies that are bound to marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems. For example, one or more labels can be attached to the antibody, thereby permitting detection of the target protein (i.e the marker). Exemplary labels include radioactive isotopes, fluorophores, ligands, chemiluminescent agents, enzymes, and combinations thereof. In some embodiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. $^{3}H$, $^{14}C$, $^{32}P$, $^{35}S$ or $^{125}I$) and particles (e.g. gold). The resulting stained specimens may be imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the marker in the sample. Various automated sample processing, scanning and analysis systems suitable for use with immunohistochemistry are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549).

In some embodiments, detecting the expression of SLITRK6 is determined by detecting the quantity of mRNA encoding for SLITRK6. Methods for determining the quantity of mRNA are well known in the art. For example the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. The extracted mRNA is then detected by hybridization (e. g., Northern blot analysis, in situ hybridization) and/or amplification (e.g., RT-PCR). Other methods of Amplification include ligase chain reaction (LCR), transcription-mediated amplification (TMA), strand displacement amplification (SDA) and nucleic acid sequence based amplification (NASBA). Typically, the nucleic acid probes include one or more labels, for example to permit detection of a target nucleic acid molecule using the disclosed probes. Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials. Particular examples of detectable labels include fluorescent molecules (or fluorochromes). Numerous fluorochromes are known to those of skill in the art, and can be selected, for example from Life Technologies (formerly Invitrogen), e.g., see, The Handbook-A Guide to Fluorescent Probes and Labeling Technologies). Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH). Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. 0.1. Pathol. 157:1467-1472, 2000 and U.S. Pat. No. 6,942,970. Additional detection methods are provided in U.S. Pat. No. 6,280,929.

The invention will be further illustrated by the following figures and examples. However, these examples and figures should not be interpreted in any way as limiting the scope of the present invention.

FIGURES

Figure 1A:
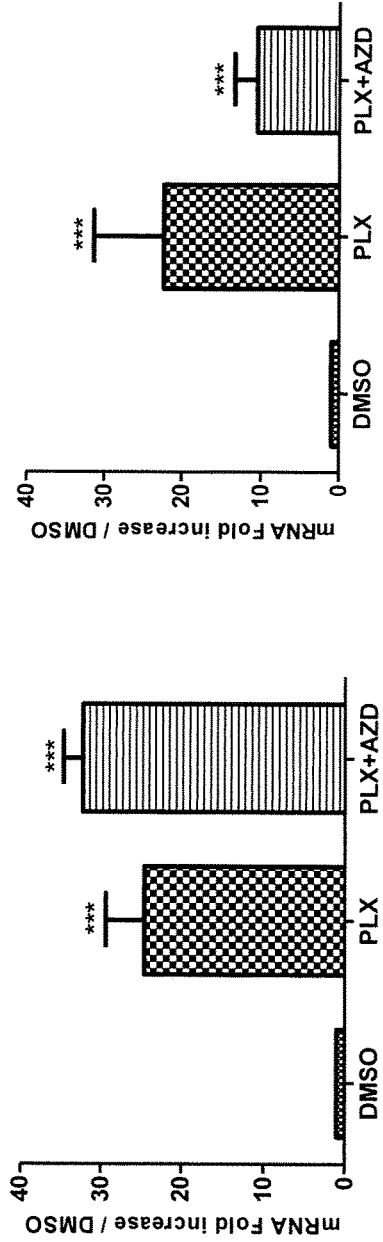
Figure 1B:
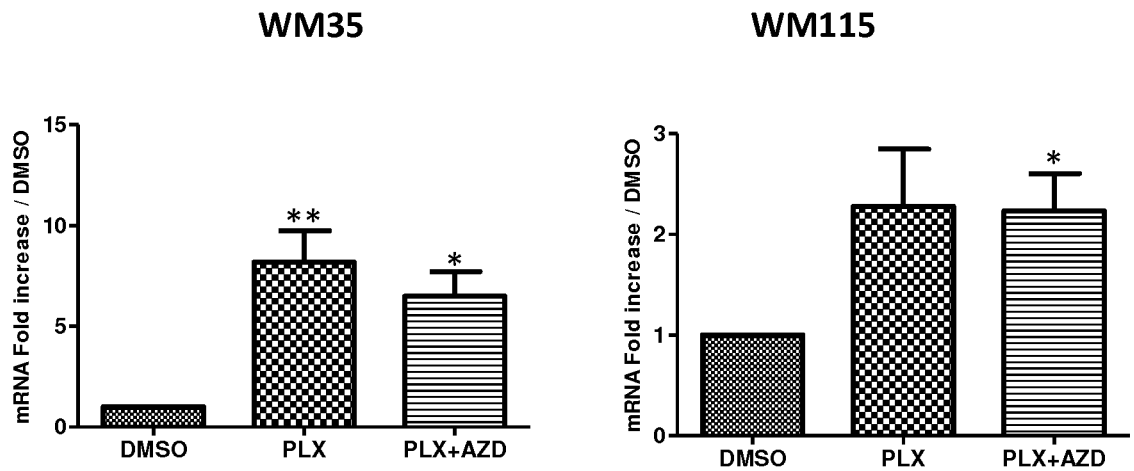

FIG. 1. SLITRK6 mRNA expression is induced under MAPK inhibitor treatment in BRAF-mutant melanoma cells. A) A375, Lu1205, WM266-4 and WM983B cell lines were treated with a BRAF inhibitor (PLX4032) at 1 µM alone or in combination with a 0.1 µM MEK inhibitor (AZD6244). mRNA fold increase relative to the DMSO control is determined by Q-PCR. The results are presented as the mean±SD of the average of 3 independent experiments. * $p<0.001$; T-test. B) BRAF-mutant melanoma cells lines WM35 and WM115 were treated with a BRAF inhibitor (PLX4032, 1 µM) alone or in combination with a MEK inhibitor (AZD6244, 0.1 µM) for 72 h and SLITRK6 mRNA was analyzed by RT-qPCR. Data shown are the means±standard deviation of 3 independent experiments.  $p<0.01$; * $p<0.05$; t-test.

Figure 2:
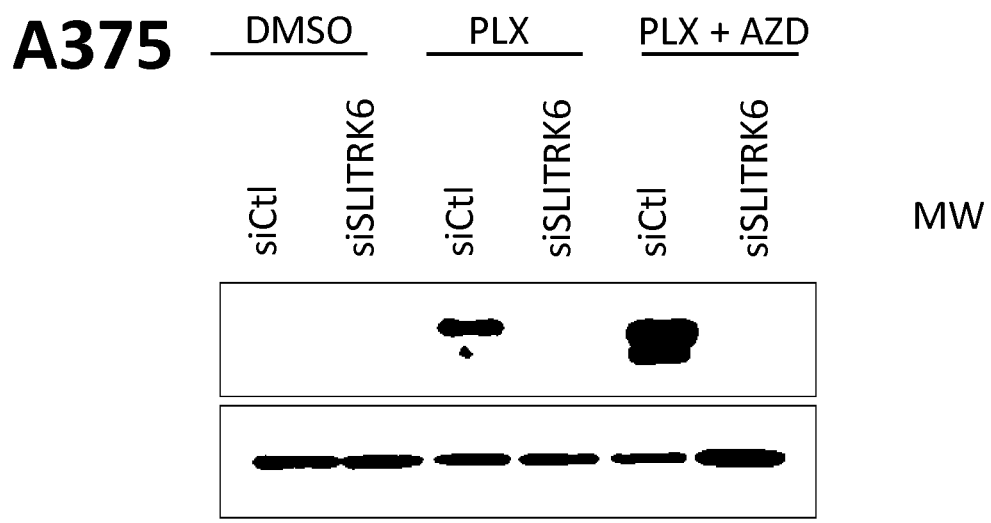
Figure 2:
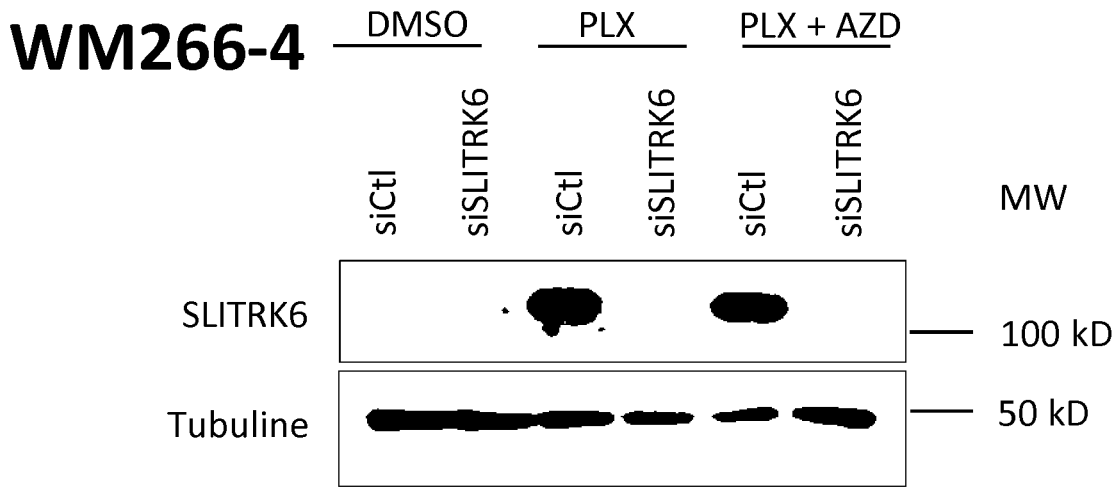

FIG. 2. siRNA directed against SLITRK6 inhibit its expression of in metastatic melanoma cell lines. A375 and WM266-4 cells lines are first transfected with siRNAs against SLITRK6 or control siRNAs and then treated with PLX4032 at 1 µM alone or in combination with the AZD6244 at 0.1 µM for 72 h. The expression of SLITRK6 is analyzed by Western Blot. Tubulin is used as loading control.

Figure 3:
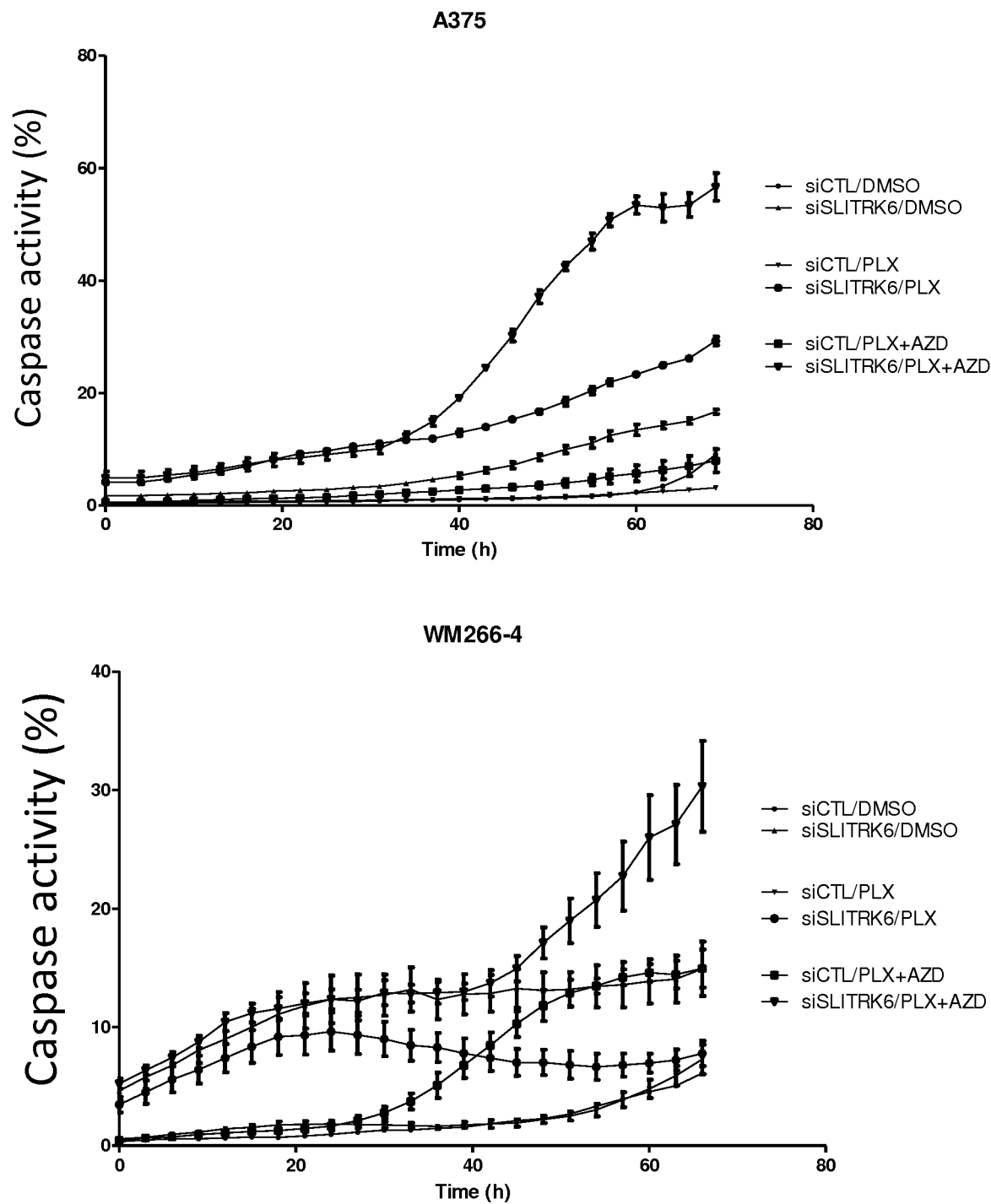

FIG. 3. Concurrent inhibition of MAPK pathway and SLITRK6 triggers apoptosis in BRAF-mutant melanoma cells. A375 and WM266-4 cell lines are first transfected with siRNAs specific for SLITRK6 or control siRNAs and then treated with PLX4032 at 1 µM alone or in combination with the AZD6244 at 0.1 µM for 72 h. The kinetics of activation of caspases 3 and 7 over time is monitored by fluorescence using Incucyte®. The data are standardized with respect to the number of cells per well at the end of the experiment. These results are representative of 2 experiments.

Figure 4:
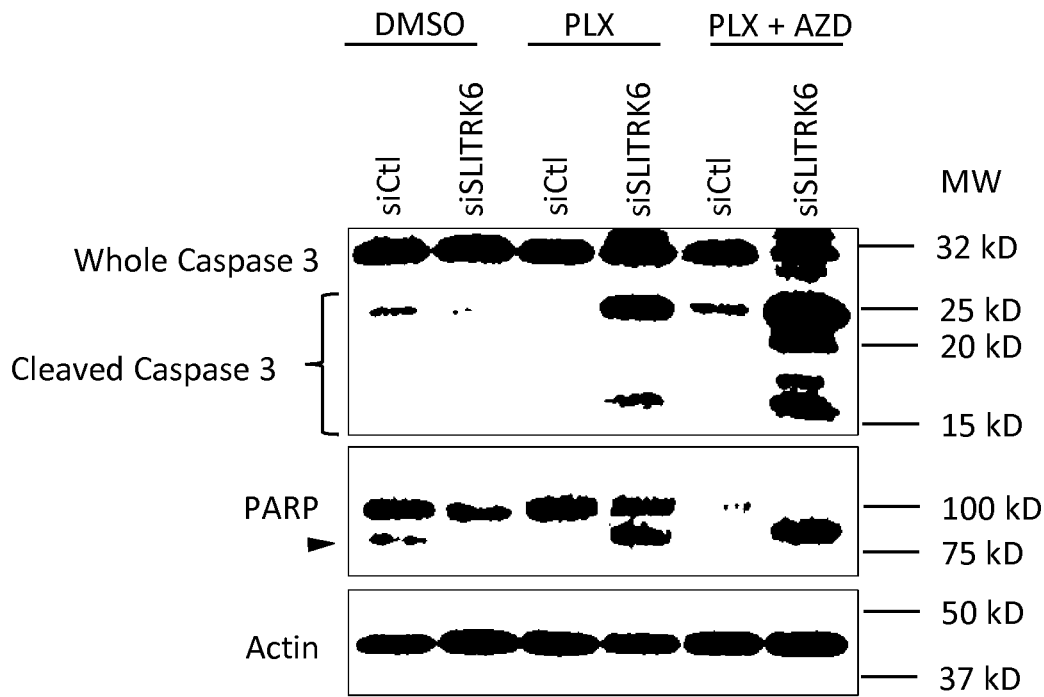
Figure 4:
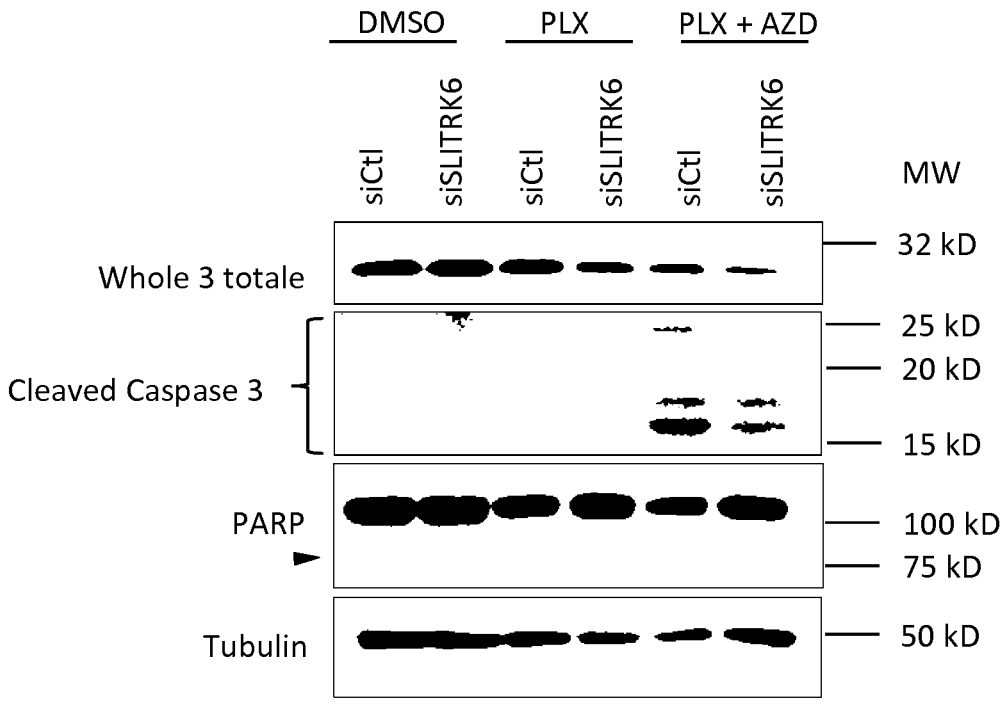

FIG. 4. Concurrent inhibition of MAPK pathway and SLITRK6 triggers apoptosis in BRAF-mutant melanoma cells. A375 and WM266-4 cell lines are first transfected with siRNAs specific for SLITRK6 or control siRNAs and then treated with PLX4032 at 1 µM alone or in combination with the AZD6244 at 0.1 µM for 72 h. Cleavages of caspase 3 and PARP are analyzed by Western Blot. Tubulin and actinare used as loading control. These results are representative of 3 experiments.

Figure 5:
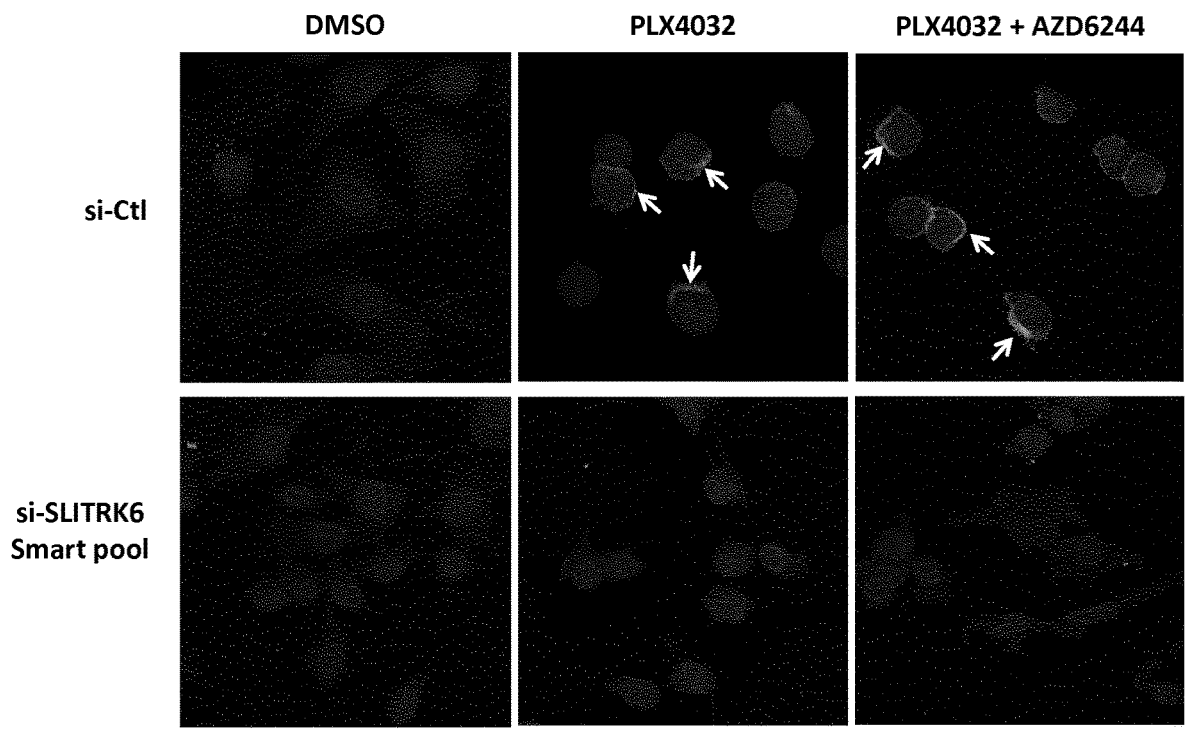

FIG. 5. The antibody against SLITRK6 binds its target specifically at the membrane only after MAPK inhibitor treatment. A375 cells were transfected with siRNA control (si-Ctl) or targeting SLITRK6 (si-SLITRK6) before treatment with PLX4032 (1 µM) alone or in combination with AZD6244 (0.1 µM) for 48 h. Cells were then stained for SLITRK6 (green) and DNA was counterstained with DAPI (blue). These results are representative of 3 independent experiments.

Figure 6:
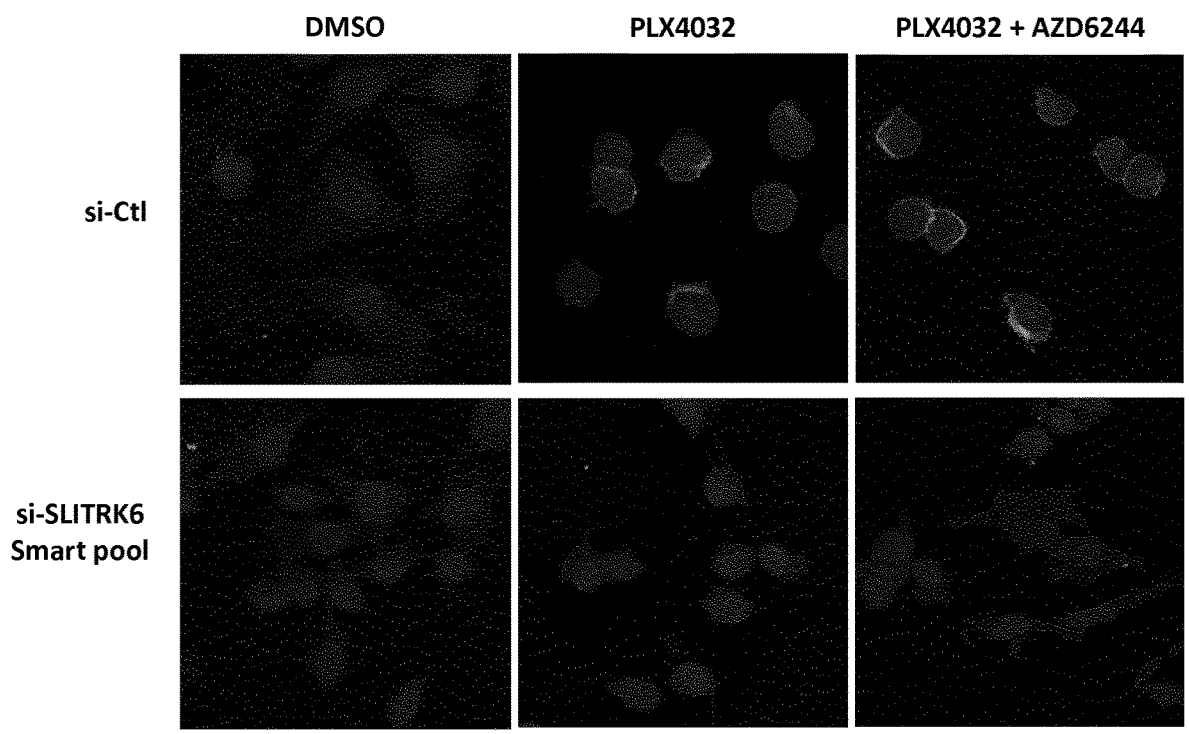

FIG. 6. The antibody against SLITRK6 internalizes its target specifically only after MAPKi treatment. A375 cells were transfected with siRNA control (si-Ctl) or targeting SLITRK6 (si-SLITRK6) before treatment with PLX4032 (1 µM) alone or in combination with AZD6244 (0.1 µM) for 48 h. Cells were then stained for SLITRK6 (green) and DNA was counterstained with DAPI (blue). These results are representative of 3 independent experiments.

Figure 7:
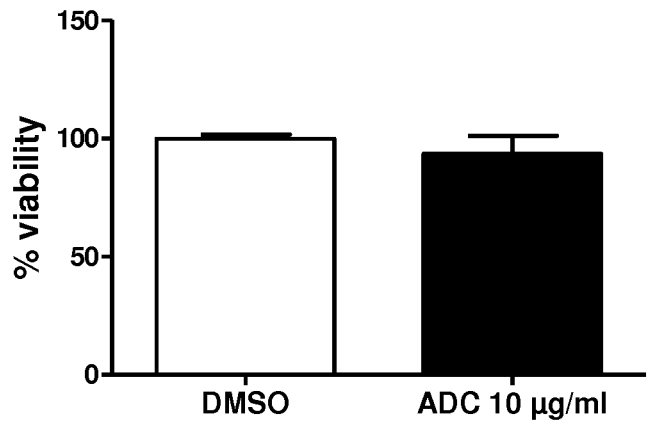
Figure 8A:
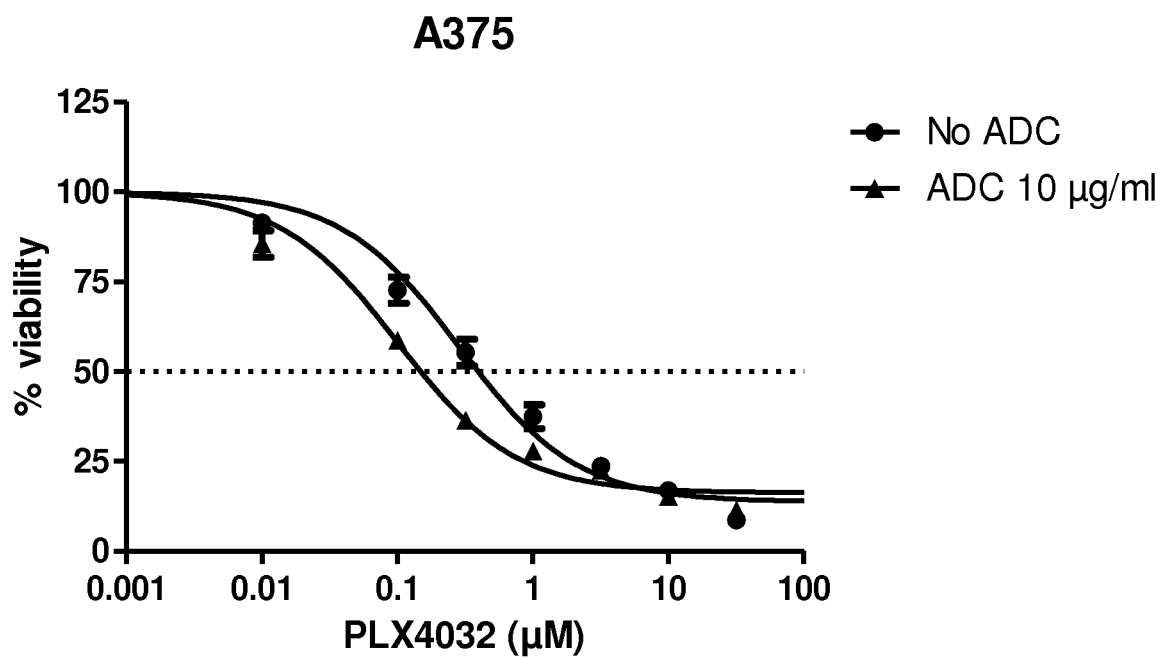
Figure 8B:
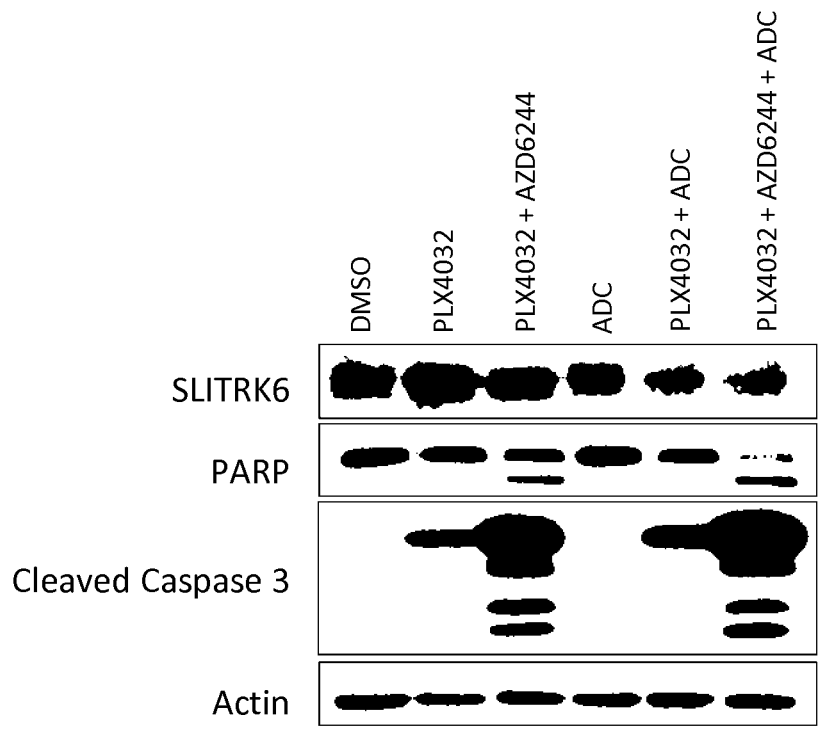
Figure 8C:
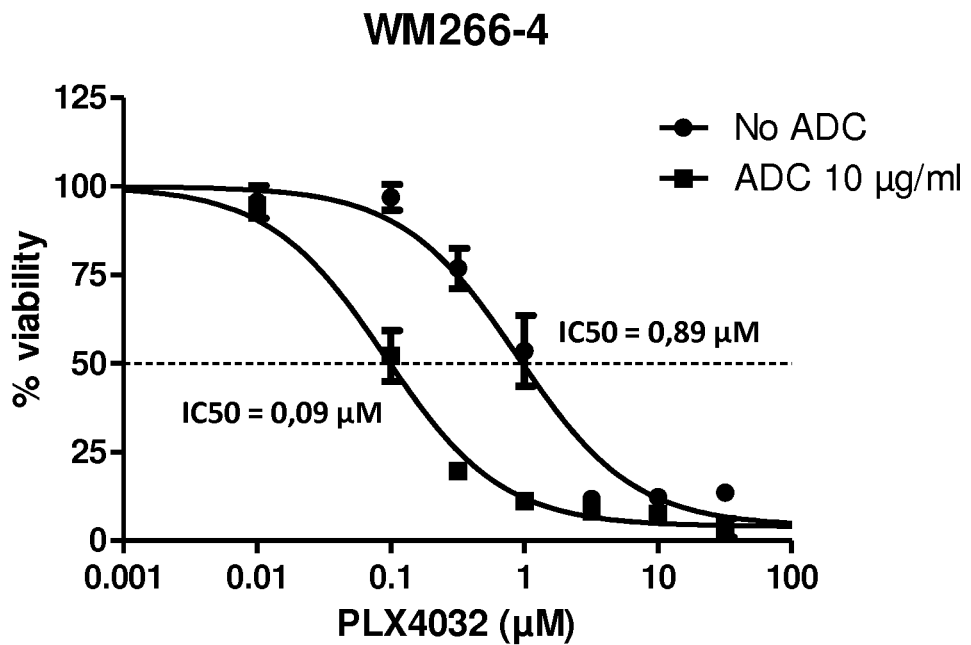
Figure 8D:
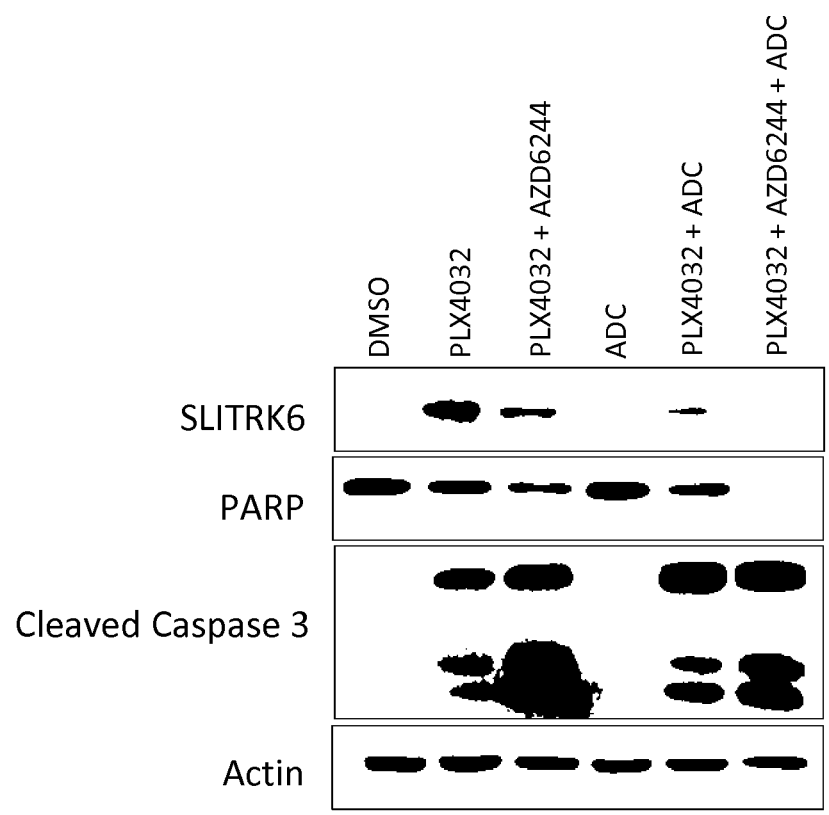

FIG. 7. MMAE-conjugated antibody against SLITRK6 has no effect on cells' viability alone. WM266-4 cells were treated for 72 h with DMSO or with antibody drug-conjugated against SLITRK6 (ADC) at 10 µg/mL. Cell viability was measured by MTS. Data shown are the means±standard deviation of triplicates of 1 experiment.

FIG. 8. MMAE-conjugated antibody against SLITRK6 sensitizes cells to PLX4032 in two cell lines (A375 and WM266-4). A. A375 cells were treated for 72 h with PLX4032 alone or in combination with antibody drug-conjugated against SLITRK6 (ADC) at 10 µg/mL. Cell viability was measured by MTS and the dose-response was analyzed. Data shown are the means±standard deviation of triplicates of 1 experiment. B. A375 cells were treated for 48 h with PLX4032 at 1 µM alone or in combination with antibody drug-conjugated against SLITRK6 (ADC) at 10 µg/mL or in combination with AZD6244 at 0.1 µM. Cleaved caspase-3 and cleaved PARP were analyzed by Western blotting. Expression of SLITRK6 was analyzed in parallel. Actin was the loading control. C. WM266-4 cells were treated for 72 h with PLX4032 alone or in combination with antibody drug-conjugated against SLITRK6 (ADC) at 10 µg/mL. Cell viability was measured by MTS and the dose-response was analyzed. Data shown are the means±standard deviation of triplicates of 1 experiment. D. WM266-4 cells were treated for 48 h with PLX4032 at 1 µM alone or in combination with antibody drug-conjugated against SLITRK6 (ADC) at 10 µg/mL or in combination with AZD6244 at 0.1 µM. Cleaved caspase-3 and cleaved PARP were analyzed by Western blotting. Expression of SLITRK6 was analyzed in parallel. Actin was the loading control.

EXAMPLE

The response of subjects suffering from a BRAF-mutated cancer to BRAF inhibitors is dramatically impaired by secondary resistances and rapid relapse. So far, the molecular mechanisms driving these resistances are not completely understood. Recently we showed that, inhibition of BRAF or its target MEK in BRAF-mutant melanoma cell lines induces RHOB expression by a mechanism that depends on the transcription factor c-Jun (Oncotarget. 2015 Jun. 20; 6(17):15250-64). More particularly our findings reveal that BRAF inhibition activates a c-Jun/RHOB/AKT pathway that promotes tumor cell survival and further support a role of this pathway in the resistance of melanoma to vemurafenib. Following transcriptomic analyses we showed that activation of c-Jun induces the expression of SLITRK6 (SLIT and NTRK-like family, member 6). In particular, we demonstrate that SLITRK6 expression is induced by Vemurafenib (PLX4032) (FIG. 1). Furthermore the inhibition of its induction leads to apoptotic cell death (FIGS. 3 and 4) putting on light a synthetic lethal pathway through simultaneous BRAF (or MAPK pathway) inhibition and SLITRK6 down regulation. Thus, inhibition of SLITRK6 by an inhibitor of activity or expression should potentiate the antitumor effect of MAPK inhibitors and avoid the emergence of a resistance to MAPK inhibitors. Furthermore the specific expression of the protein also paves the way of strategies based on depletion of the residual cancer cells by targeting them with anti-SLITRK6 antibodies capable of mediating ADCC or antibody-drug conjugates binding to SLITRK6. In that aim, we show that the Hal5-10acl2 antibody directed against SLITRK6 binds to melanoma cells only when the cells are treated with a MAMPK inhibitor. Furthermore, we show that the antibody internalizes the tumor cells only after a treatment with a MAPK inhibitor. Finally, we show into two cell lines that the antibody conjugated to monomethyl auristatin E (MMAE) sensitizes the tumor cells to MAPK inhibitors. Accordingly, the results demonstrate that anti SLITRK6 antibody-drug conjugate in combination with MAPK inhibitors lead to synthetic lethality showing that the combination would be suitable for the treatment of cancers associated with activation of the MAPK pathway.

REFERENCES

Throughout this application, various references describe the state of the art to which this invention pertains. The disclosures of these references are hereby incorporated by reference into the present disclosure.

The invention claimed is:

1. A method of treating a cancer characterized by at least one mutation in the MAPK pathway in a subject in need thereof, comprising
    administering to the subject a therapeutically effective combination comprising
    at least one MAPK inhibitor and
    an agent that inhibits activity of SLITRK6 and mediates cell death of SLITRK6 expressing cancer cells, wherein the agent is
        an antibody comprising heavy and light chain variable regions of an antibody designated Hal5-10ac12 produced by a Chinese Hamster Ovary (CHO) cell deposited under the American Type Culture Collection (ATCC) Accession No.: PTA-13102, wherein the heavy chain variable region of Hal5-10ac12 has the amino acid as set forth in SEQ ID NO:1, and the light chain variable region of Hal5-10ac12 has the amino acid sequence as set forth in SEQ ID NO:2, or
        a drug conjugate comprising the antibody.

2. The method of claim 1 wherein the at least one mutation is in NRAS or BRAF.

3. The method of claim 1 wherein the subject suffers from a cancer selected from the group consisting of melanoma, multiple myeloma, lung cancer, colorectal cancer, thyroid carcinoma, blood cancer, leukemia, and lymphoma.

4. The method of claim 1 wherein the MAPK inhibitor is selected from the group consisting of MEK inhibitors and BRAF inhibitors.

5. The method of claim 1 wherein the therapeutically effective combination comprises a BRAF inhibitor, a MEK inhibitor and the agent that inhibits activity of SLITRK6 and mediates cell death of SLITRK6 expressing cancer cells.

6. The method of claim 1 wherein the at least one MAPK inhibitor is vemurafenib.

7. The method of claim 1 wherein the antibody has binding affinity for SLITRK6.

8. The method of claim 7 wherein the antibody mediates antibody-dependent cell-mediated cytotoxicity.

9. The method of claim 7 wherein the antibody is conjugated to an auristatin or an auristatin peptide analog, an auristatin derivative or an auristatin prodrug thereof.

10. A method of determining and treating relapse in a subject suffering from a cancer after a treatment regimen comprising administration of a MAPK inhibitor, comprising
    i) detecting the expression of SLITRK6 in a tumor sample obtained from the subject;
    ii) concluding that the subject has relapsed when the expression of SLITRK6 is detected at step i); and
    iii) administering to the subject a therapeutically effective combination comprising at least one MAPK inhibitor and an agent that inhibits activity of SLITRK6 and mediates cell death of SLITRK6 expressing cancer cells, wherein the agent is
        an antibody comprising heavy and light chain variable regions of an antibody designated Hal5-10ac12 produced by a Chinese Hamster Ovary (CHO) cell deposited under the American Type Culture Collection (ATCC) Accession No.: PTA-13102, wherein the heavy chain variable region of Hal5-10ac12 has the amino acid as set forth in SEQ ID NO:1, and the light chain variable region of Hal5-10ac12 has the amino acid sequence as set forth in SEQ ID NO:2, or
        a drug conjugate comprising the antibody.

11. The method of claim 10 wherein the tumor sample is from a tumor resected from the subject or is from a biopsy performed in the primary tumor of the subject or a metastasis distant from the primary tumor of the subject, or is a sample of circulating tumor cells.

12. The method of claim 10 wherein the step of detecting is performed by detecting the quantity of mRNA encoding for SLITRK6 or by immunodetection of SLITRK6 protein.

* * * * *

SEQUENCE LISTING

```
<160> NUMBER OF SEQ ID NOS: 2

<210> SEQ ID NO 1
<211> LENGTH: 120
<212> TYPE: PRT
<213> ORGANISM: Artificial
<220> FEATURE:
<223> OTHER INFORMATION: Synthetic heavy chain variable region of
      Hal5-10acl2

<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Gln Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met His Ser Leu Arg Ala Glu Asp Thr Ala Val Tyr Tyr Cys
                85                  90                  95

Ala Arg Gly Leu Thr Ser Gly Arg Tyr Gly Met Asp Val Trp Gly Gln
            100                 105                 110

Gly Thr Thr Val Thr Val Ser Ser
        115                 120

<210> SEQ ID NO 2
<211> LENGTH: 113
<212> TYPE: PRT
<213> ORGANISM: Artificial
<220> FEATURE:
<223> OTHER INFORMATION: Synthetic light chain variable region of
      Hal5-10acl2

<400> SEQUENCE: 2

Asp Ile Val Met Thr Gln Ser Pro Leu Ser Leu Pro Val Thr Pro Gly
1               5                   10                  15
```

-continued

```
Glu Pro Ala Ser Ile Ser Cys Arg Ser Ser Gln Ser Leu Leu Leu Ser
            20                  25                  30

His Gly Phe Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Pro
                85                  90                  95

Leu Gln Ile Pro Trp Thr Phe Gly Gln Gly Thr Lys Val Glu Ile Lys
            100                 105                 110

Arg
```